(12) United States Patent
Berger et al.

(10) Patent No.: US 7,202,241 B2
(45) Date of Patent: *Apr. 10, 2007

(54) BENZOXAZINE DERIVATIVES AND USES THEREOF

(75) Inventors: Jacob Berger, Los Altos Hills, CA (US); Robin Douglas Clark, Lawai, HI (US); Shu-Hai Zhao, Sunnyvale, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 90 days.

This patent is subject to a terminal disclaimer.

(21) Appl. No.: 11/008,310

(22) Filed: Dec. 9, 2004

(65) Prior Publication Data

US 2005/0124613 A1    Jun. 9, 2005

Related U.S. Application Data

(60) Provisional application No. 60/528,378, filed on Dec. 9, 2003.

(51) Int. Cl.
*C07D 413/04* (2006.01)
*C07D 413/14* (2006.01)
*A61K 31/536* (2006.01)

(52) U.S. Cl. .................. 514/230.5; 544/105
(58) Field of Classification Search .......... 544/105; 514/230.5
See application file for complete search history.

(56) References Cited

U.S. PATENT DOCUMENTS 6,867,204 B2 *  3/2005  Berger et al. ......... 514/211.09

FOREIGN PATENT DOCUMENTS

| WO | WO 89/07596 A1 | 8/1989 |
|---|---|---|
| WO | WO 96/31508 A1 | 10/1996 |
| WO | WO 98/50358 A1 | 11/1998 |
| WO | WO 00/66564 A1 | 11/2000 |
| WO | WO 01/16108 A2 | 3/2001 |
| WO | WO 01/57003 A1 | 8/2001 |
| WO | WO 03/095434 A1 | 11/2003 |
| WO | WO 2004/041792 A | 5/2004 |

OTHER PUBLICATIONS

Thomas A. Godwin (Gastrointestinal Diseases, <http://edcenter.med.cornell.edu/CUMC_PathNotes/Gastrointestinal/Gastrointestinal.html>, 51 pages), downloaded on Jul. 7, 2005.*
Russell MG and Dias R. (Curr. Top. Med. Chem, Jun. 2002; 2(6):643-654).*

* cited by examiner

*Primary Examiner*—Kahsay Habte
(74) *Attorney, Agent, or Firm*—Robert C. Hall

(57) ABSTRACT

Compounds of the formula (I):

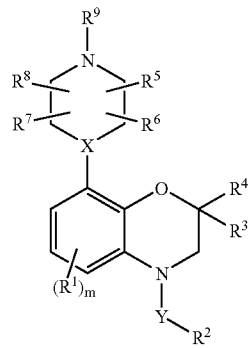

or pharmaceutically acceptable salts, solvates or prodrugs thereof, where $R^1$, $R^2$, $R^3$, $R^4$, $R^5$, $R^6$, $R^7$, $R^8$, $R^9$, X, Y and m are as defined herein. Also provided are compositions comprising, methods for using, and methods for preparing compound of formula (I).

18 Claims, No Drawings

BENZOXAZINE DERIVATIVES AND USES THEREOF

CROSS REFERENCE TO RELATED APPLICATIONS

This application claims benefit under 35 U.S.C. 119(e) of U.S. Provisional Application No. 60/528,378 filed Dec. 9, 2003, which is hereby incorporated by reference in its entirety.

FIELD OF THE INVENTION

This invention relates to benzoxazine derivatives, and associated compositions, methods for use as therapeutic agents, and methods of preparation thereof.

BACKGROUND OF THE INVENTION

The actions of the neurotransmitter 5-hydroxytryptamine (5-HT) as a major modulatory neurotransmitter in the brain, are mediated through a number of receptor families termed 5-HT1, 5-HT2, 5-HT3, 5-HT4, 5-HT5, 5-HT6, and 5-HT7. Based on a high level of 5-HT6 receptor MRNA in the brain, it has been stated that the 5-HT6 receptor may play a role in the pathology and treatment of central nerve system disorders. In particular, 5-HT2 and 5-HT6 selective ligands have been identified as potentially useful in the treatment of certain CNS disorders such as Parkinson's disease, Huntington's disease, anxiety, depression, manic depression, psychoses, epilepsy, obsessive compulsive disorders, mood disorders, migraine, Alzheimer's disease (enhancement of cognitive memory), sleep disorders, feeding disorders such as anorexia, bulimia and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain gastrointestinal (GI) disorders such as functional bowel disorder. See for example, B. L. Roth et al., *J. Pharmacol. Exp. Ther.*, 1994, 268, pages 1403–14120, D. R. Sibley et al., *Mol. Pharmacol.*, 1993, 43, 320–327, A. J. Sleight et al., *Neurotransmission*, 1995, 11, 1–5, and A. J. Sleight et al., *Serotonin ID Research Alert*, 1997, 2(3), 115–8.

While some 5-HT6 modulators have been disclosed, there continues to be a need for compounds that are useful for modulating 5-HT6 and/or the other 5-hydroxytryptamine receptors noted above.

SUMMARY OF THE INVENTION

The present invention provides compounds of the formula (I):

I or a pharmaceutically acceptable salt, solvate or prodrug thereof, wherein:

m is from 0 to 3;

X is N or CH;

Y is —SO$_2$— or —CH$_2$—;

each $R^1$ is independently halo, alkyl, haloalkyl, alkoxy, cyano, hydroxyalkyl, alkoxyalkyl, —SO$_2R^a$, —C(=O)—NR$^b$R$^c$, —SO$_2$—NR$^b$R$^c$, —SR$^b$, —N(R$^b$)—C(=O)—R$^c$, —C(=O)—R$^b$, or —N(R$^b$)—SO$_2$—R$^a$, where each $R^a$ is independently alkyl or haloalkyl, and each of $R^b$ and $R^c$ is independently hydrogen, alkyl, or haloalkyl, $R^2$ is aryl or heteroaryl;

each of $R^3$ and $R^4$ is independently alkyl, hydroxyalkyl or alkoxyalkyl, or $R^3$ and $R^4$ together with the carbon to which they are attached may form a cyclic group with 3 to 6 ring atoms that optionally includes a heteroatom selected from N, O and S; and each of $R^5$, $R^6$, $R^7$, $R^8$ and $R^9$ is independently hydrogen or alkyl, or $R^9$ and one of $R^5$, $R^6$, $R^7$, or $R^8$ together with the atoms to which they are attached form a heterocycloamino ring with 5 to 7 ring atoms.

The present invention also provides methods for preparing, compositions comprising, and methods for using compounds of Formula (I).

The subject compounds include 2,2-dialkyl substituents or other disubstitution at the 2-position of the benzoxazine ring system that surprisingly results in greater affinity for 5-hydroxytryptamine receptors, particularly 5-HT-6, than is found in compounds wherein only hydrogen is present at the 2-position of the benzoxazine ring system.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Agonist" refers to a compound that enhances the activity of another compound or receptor site.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" means a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^aR^b$—wherein $R^a$ is alkoxy as defined herein and $R^b$ is alkylene as defined herein. Exemplary alkoxyalkyl moieties include methoxyethyl, ethoxyethyl, 2,3-dimethoxypropyl and the like.

"Antagonist" refers to a compound that diminishes or prevents the action of another compound or receptor site.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof.

"Arylalkyl" and "Aralkyl", which may be used interchangeably, mean a radical —$R^aR^b$ where $R^a$ is an alkylene group and $R^b$ is an aryl group as defined herein; e.g., benzyl, phenylethyl, 3-(3-chlorophenyl)-2-methylpentyl, and the like are examples of arylalkyl.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Cycloalkylalkyl" means a moiety of the formula —R'—R", where R' is alkylene and R" is cycloalkyl as defined herein.

"Heteroalkyl" means an alkyl radical as defined herein wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, aminosulfonylpropyl, methylaminosulfonylmethyl, methylaminosulfonylethyl, methylaminosulfonylpropyl, and the like.

"Hydroxyalkyl" means a moiety of the formula HO—$R^c$— wherein $R^c$ is alkylene as defined herein. Exemplary hydroxyalkyl moieties include hydroxyethyl, hydroxypropyl, 2,3-dihydroxypropyl and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuiryl, benzothiophenyl, benzothiopyranyl, benzimidazolyl, benzoxazolyl, benzoxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

The terms "halo" and "halogen", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofliryl, tetrahydrofliryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like.

"Optionally substituted", when used in association with "aryl", "phenyl", "heteroaryl" or "heterocyclyl", means an aryl, phenyl, heteroaryl or heterocyclyl which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, monoalkylamino, di-alkylamino, haloalkyl, haloalkoxy, heteroalkyl, —COR (where R is hydrogen, alkyl, phenyl or phenylalkyl), —$(CR'R")_n$—COOR (where n is an integer from 0 to 5, R'and R" are independently hydrogen or alkyl, and R is hydrogen, alkyl, cycloalkyl, cycloalkylalkyl, phenyl or phenylalkyl), or —$(CR'R")_n$—$CONR^aR^b$ (where n is an integer from 0 to 5, R' and R" are independently hydrogen or alkyl, and $R^a$ and $R^b$ are, independently of each other, hydrogen, alkyl, cycloalkyl, cycloalkylalkyl, phenyl or phenylalkyl).

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease state" means any disease, condition, symptom, or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound. Such salts include:

acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic, camphorsulfonic acid, citric acid, ethanesulfonic acid, fumaric acid, glucoheptonic acid, gluconic acid, glutamic acid, glycolic acid, hydroxynaphtoic acid, 2-hydroxyethanesulfonic acid, lactic acid, maleic acid, malic acid, malonic acid, mandelic acid, methanesulfonic acid, muconic acid, 2-naphthalenesulfonic acid, propionic acid, salicylic acid, succinic acid, tartaric acid, p-toluenesulfonic acid, trimethylacetic acid, and the like; or salts formed when an acidic proton present in the parent compound either is replaced by a metal ion, e.g., an alkali metal ion, an alkaline earth ion, or an aluminum ion; or coordinates with an organic or inorganic base. Acceptable organic bases include diethanolamine, ethanolamine, N-methylglucarnine, triethanolamine, tromethamine, and the like.

Acceptable inorganic bases include aluminum hydroxide, calcium hydroxide, potassium hydroxide, sodium carbonate and sodium hydroxide.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium.

It should be understood that all references to pharmaceutically acceptable salts include solvent addition forms (solvates) or crystal forms (polymorphs) as defined herein, of the same acid addition salt.

The terms "pro-drug" and "prodrug", which may be used interchangeably herein, refer to any compound which releases an active parent drug according to formula I in vivo when such prodrug is administered to a mammalian subject. Prodrugs of a compound of formula I are prepared by modifying one or more functional group(s) present in the compound of formula I in such a way that the modification(s) may be cleaved in vivo to release the parent compound. Prodrugs include compounds of formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of formula I, N-acyl derivatives (e.g. N-acetyl) N-Mannich bases, Schiff bases and enaminones of amino functional groups, oximes, acetals, ketals and enol esters of ketone and aldehyde functional groups in compounds of Formula I, and the like, see Bundegaard, H. "Design of Prodrugs" p1–92, Elesevier, New York-Oxford (1985), and the like.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to chose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgement of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:
(i) preventing the disease state, i.e. causing the clinical symptoms of the disease state not to develop in a subject that may be exposed to or predisposed to the disease state, but does not yet experience or display symptoms of the disease state.
(ii) inhibiting the disease state, i.e., arresting the development of the disease state or its clinical symptoms, or
(iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature used in this Application is based on AUTONOM™ v.4.0, a Beilstein Institute computerized system for the generation of IUPAC systematic nomenclature. For convenience, the IUPAC numbering of the positions of representative benzoxazine compounds described herein is shown by the formula:

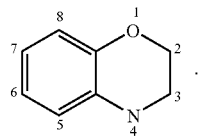

Chemical structures shown herein were prepared using ISIS® v.2.2. Any open valency on a carbon, nitrogen or oxygen atom on the chemical structures herein should be understood as indicating the presence of a hydrogen.

Compounds of the Invention

The invention provides compounds of the formula (I):

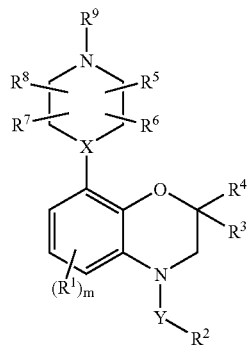

I or a pharmaceutically acceptable salt, solvate or prodrug thereof, wherein:

m is from 0 to 3; preferably m is 0 or 1;

X is N or CH; preferably X is N;

Y is —$SO_2$— or —$CH_2$—; preferably Y is —$SO_2$—;

each $R^1$ is independently halo, alkyl, haloalkyl, alkoxy, cyano, hydroxyalkyl, alkoxyalkyl, —$SO_2R^a$, —C(=O)—$NR^bR^c$, —$SO_2$—$NR^bR^c$, —$SR^b$, —$N(R^b)$—C(=O)—$R^c$, —C(=O)—$R^b$, or —$N(R^b)$—$SO_2$—$R^a$, where
each $R^a$ is independently alkyl or haloalkyl, and
each of $R^b$ and $R^c$ is independently hydrogen, alkyl, or haloalkyl;

$R^2$ is aryl or heteroaryl;

each of $R^3$ and $R^4$ is independently alkyl, hydroxyalkyl or aLkoxyalkyl, or $R^3$ and $R^4$ together with the carbon to which they are attached may form a cyclic group with 3 to 6 ring atoms that optionally includes a heteroatom selected from N, O and S; preferably $R^3$ and $R^4$ are alkyl; and each of $R^5$, $R^6$, $R^7$, $R^8$ and $R^9$ is independently hydrogen or alkyl, or $R^9$ and one of $R^5$, $R^6$, $R^7$, or $R^8$ together with the atoms to which they are attached form a heterocycloamino ring with 5 to 7 ring atoms.

It is to be understood that the scope of this invention encompasses not only the various isomers which may exist but also the various mixture of isomers which may be formed. Furthermore, the scope of the present invention also encompasses solvates and salts of Compounds of Formula I. Where any of $R^1$, $R^3$, $R^4$, $R^5$, $R^6$, $R^7$, $R^8$ and $R^9$ are alkyl, they are preferably lower alkyl, i.e. $C_1$–$C_6$ alkyl, and more preferably $C_1$–$C_4$ alkyl.

In certain embodiments, $R^2$ may be optionally substituted phenyl or optionally substituted naphthyl. More preferably, $R^2$ is phenyl, 2-fluorophenyl, 2-chlorophenyl, 3,4-dichlorophenyl, 4-chlorophenyl, 3-chlorophenyl, 4-methoxyphenyl, 3,5-dichlorophenyl, 2,6-dichlorophenyl, 2,4-dichlorophenyl, 3-methanesulfonylaminophenyl, 2-methanesulfonylphenyl, 2-carbamoylphenyl, 3-methanesulfonylphenyl, 4-methanesulfonylphenyl, 3-fluorophenyl, naphthyl, 2,4-difluorophenyl, 2-cyanophenyl, 2-chloro-4-fluorophenyl, 2-methyl-5-fluorophenyl, or 5-chloronaphthyl. In specific embodiments, $R^2$ phenyl or halo-substituted phenyl. More preferably, $R^2$ is phenyl, or halophenyl such 2-halophenyl, 3-halophenyl or 4-halophenyl. In specific embodiments, $R^2$ may be 2-chloro-substituted phenyl or 2-fluoro-substituted phenyl.

In certain embodiments, $R^3$ and $R^4$ are alkyl. In still other embodiments, $R^3$ and $R^4$ together with the carbon to which they are attached may form a cyclic group with 3 to 6 ring atoms that optionally includes a heteroatom selected from N, O and S. In specific embodiments, $R^3$ and $R^4$ are methyl, or $R^3$ and $R^4$ together with the carbon to which they are attached may form a cyclobutyl ring or group.

In certain embodiments, compounds of formula (I) are more specifically of the formula (II):

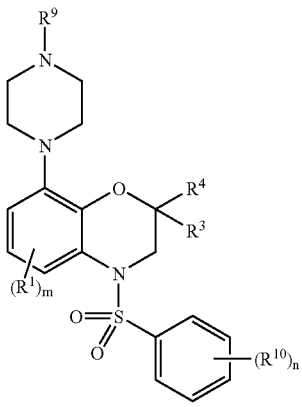

wherein:

n is from 0 to 5; preferably n is from 0 to 2;
each $R^{10}$ is independently alkyl, halo, haloalkyl, alkoxy or cyano; and
m, $R^1$, $R^3$, $R^4$ and $R^9$ are as defined herein.

Some of the representative Compounds of Formula I are shown in Table 1 below, together with melting point or mass spectrum molecular ion data. Melting points are for the corresponding hydrochloride salts unless indicated otherwise.

TABLE 1

| # | Structure | Name | Mp ° C. or M + H |
|---|-----------|------|------------------|
| 1 | 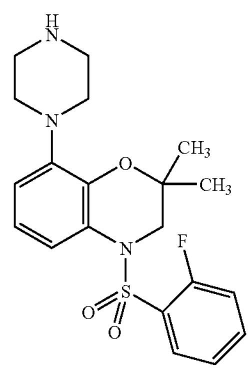 | 4-(2-Fluoro-benzenesulfonyl)-2,2-dimethyl-8-piperazin-1-yl-3,4-dihydro-2H-benzo[1,4]oxazine | 222.9–227.1° C. |
| 2 | 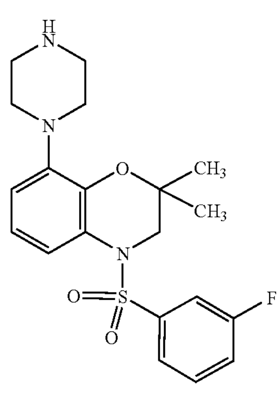 | 4-(3-Fluoro-benzenesulfonyl)-2,2-dimethyl-8-piperazin-1-yl-3,4-dihydro-2H-benzo[1,4]oxazine | >300° C. (dec.) |

TABLE 1-continued

| # | Structure | Name | Mp ° C. or M + H |
|---|-----------|------|------------------|
| 3 | 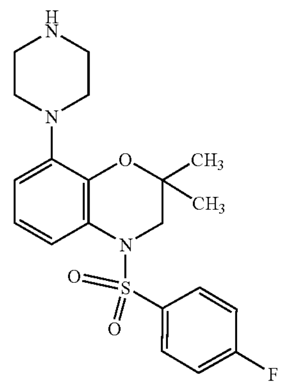 | 4-(4-Fluoro-benzenesulfonyl)-2,2-dimethyl-8-piperazin-1-yl-3,4-dihydro-2H-benzo[1,4]oxazine | 184–193° C. |
| 4 | 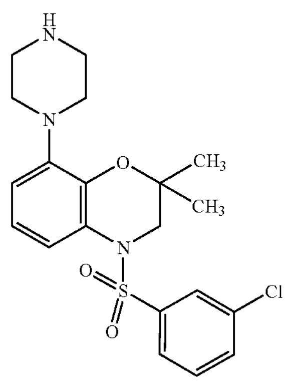 | 4-(3-Chloro-benzenesulfonyl)-2,2-dimethyl-8-piperazin-1-yl-3,4-dihydro-2H-benzo[1,4]oxazine | 233.2–235° C. |
| 5 | 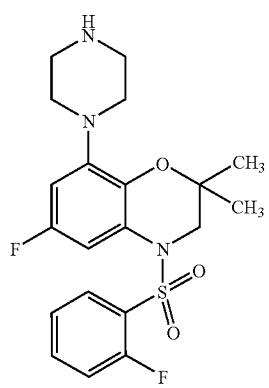 | 6-Fluoro-4-(2-fluoro-benzenesulfonyl)-2,2-dimethyl-8-piperazin-1-yl-3,4-dihydro-2H-benzo[1,4]oxazine | 262.3–265.8° C. |
| 6 | 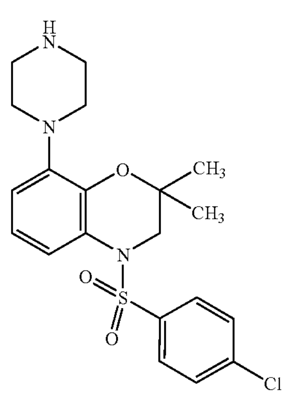 | 4-(4-Chloro-benzenesulfonyl)-2,2-dimethyl-8-piperazin-1-yl-3,4-dihydro-2H-benzo[1,4]oxazine | 273.0–277.1° C. |

TABLE 1-continued

| # | Structure | Name | Mp ° C. or M + H |
|---|---|---|---|
| 7 | 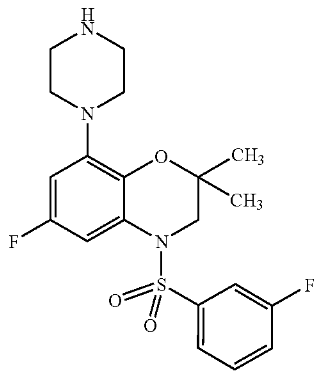 | 6-Fluoro-4-(3-fluoro-benzenesulfonyl)-2,2-dimethyl-8-piperazin-1-yl-3,4-dihydro-2H-benzo[1,4]oxazine | 197–198.2° C. |
| 8 | 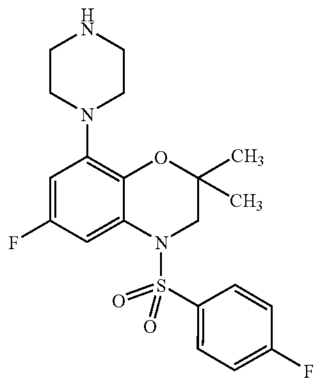 | 6-Fluoro-4-(4-fluorobenzenesulfonyl)-2,2-dimethyl-8-piperazin-1-yl-3,4-dihydro-2H-benzo[1,4]oxazine | 204.7–210.3° C. |
| 9 | 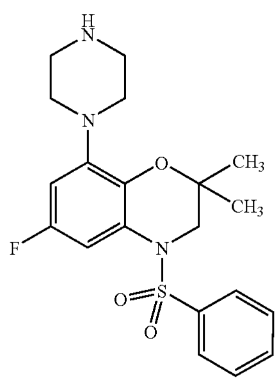 | 4-Benzenesulfonyl-6-fluoro-2,2-dimethyl-8-piperazin-1-yl-3,4-dihydro-2H-benzo[1,4]oxazine | 259.6–264.2° C. |
| 10 | 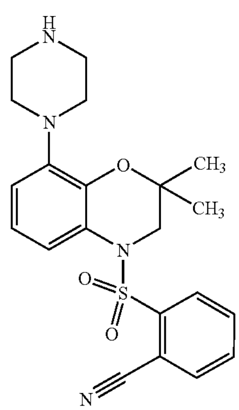 | 2-(2,2-Dimethyl-8-piperazin-1-yl-2,3-dihydro-benzo[1,4]oxazine-4-sulfonyl)-benzonitrile | 190.6–192.2° C. |

TABLE 1-continued

| # | Structure | Name | Mp ° C. or M + H |
|---|---|---|---|
| 11 | 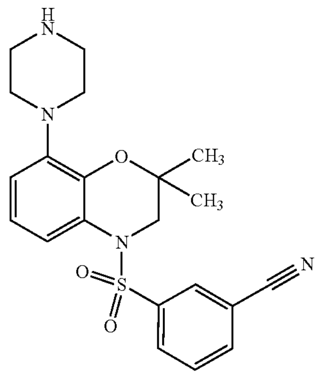 | 3-(2,2-Dimethyl-8-piperazin-1-yl-2,3-dihydro-benzo[1,4]oxazine-4-sulfonyl)-benzonitrile | 189.0–194.9° C. |
| 12 | 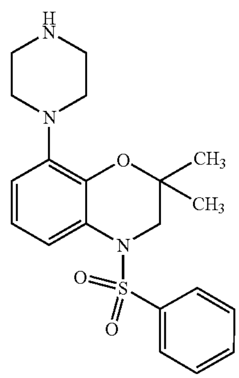 | 4-Benzenesulfonyl-2,2-dimethyl-8-piperazin-1-yl-3,4-dihydro-2H-benzo[1,4]oxazine | 213.6–215.0° C. |
| 13 | 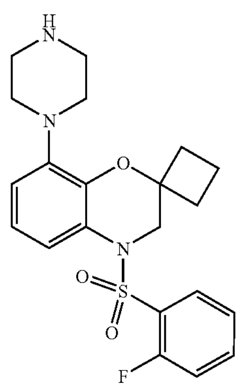 | 4-(2-Fluoro-benzenesulfonyl)-2,2-spiro-cyclobutan-8-piperazin-1-yl-3,4-dihydro-2H-benzo[1,4]oxazine | 194.8–207.6° C. |
| 14 | 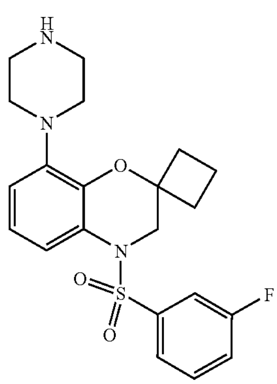 | 4-(3-Fluoro-benzenesulfonyl)-2,2-spiro-cyclobutan-8-piperazin-1-yl-3,4-dihydro-2H-benzo[1,4]oxazine | 200.1–206.1° C. |

TABLE 1-continued

| # | Structure | Name | Mp ° C. or M + H |
|---|-----------|------|------------------|
| 15 | 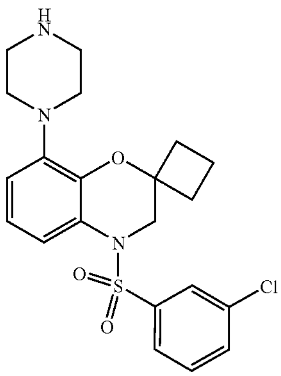 | 4-(2-Chloro-benzenesulfonyl)-2,2-spiro-cyclobutan-8-piperazin-1-yl-3,4-dihydro-2H-benzo[1,4]oxazine | 191.7–194.3° C. |
| 16 | 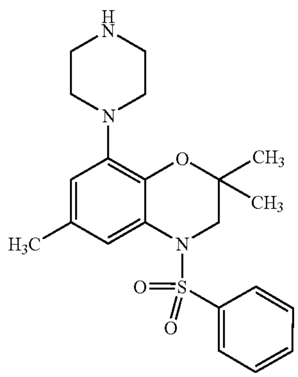 | 4-Benzenesulfonyl-2,2,6-trimethyl-8-piperazin-1-yl-3,4-dihydro-2H-benzo[1,4]oxazine | 262.9–264.6° C. |
| 17 | 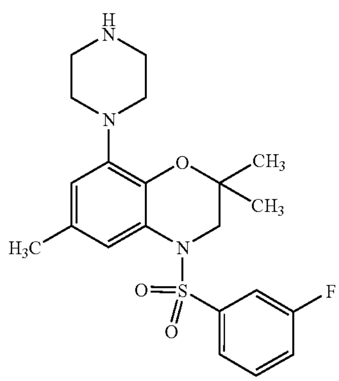 | 4-(3-Fluoro-benzenesulfonyl)-2,2,6-trimethyl-8-piperazinyl-yl-3,4-dihydro-2H-benzo[1,4]oxazine | 253.3–255.8° C. |
| 18 | 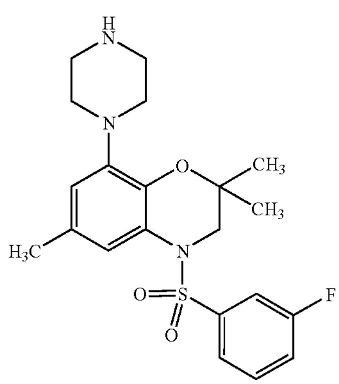 | 4-(2-Fluoro-benzenesulfonyl)-2,2,6-trimethyl-8-piperazin-1-yl-3,4-dihydro-2H-benzo[1,4]oxazine | 274.6–276.2° C. |

TABLE 1-continued

| # | Structure | Name | Mp ° C. or M + H |
|---|---|---|---|
| 19 | 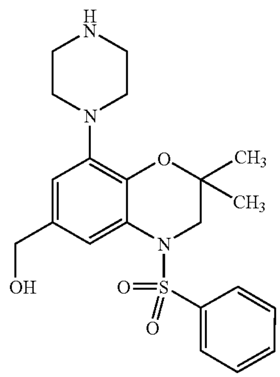 | (4-Benzenesulfonyl-2,2-dimethyl-8-piperazin-1-yl-3,4-dihydro-2H-benzo[1,4]oxazin-6-yl)-methanol | 419 (M + H) |
| 20 | 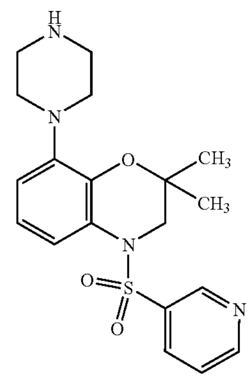 | 2,2-Dimethyl-8-piperazin-1-yl-4-(pyridine-3-sulfonyl)-3,4-dihydro-2H-benzo[1,4]oxazine | 389 (M + H) |

Another aspect of the present invention provides a composition comprising a therapeutically effective amount of a compound of formula (I) and a pharmaceutically acceptable carrier.

Yet another aspect of the present invention provides a method for treating a CNS disease state in a subject comprising administering to the subject a therapeutically effective amount of a compound of formula (I). Preferably, the disease state comprises psychoses, schizophrenia, manic depressions, neurological disorders, memory disorders, attention deficit disorder, Parkinson's disease, amyotrophic lateral sclerosis, Alzheimer's disease and Huntington's disease.

Still another aspect of the present invention provides a method for treating a disorder of the gastrointestinal tract in a subject comprising administering to the subject a therapeutically effective amount of a compound of formula (I).

Another aspect of the present invention provides a method for producing a compound of formula (I).

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1–15; *Rodd's Chemistry of Carbon Compounds*, Elsevier Science Publishers, 1989, Volumes 1–5 and Supplementals; and *Organic Reactions*, Wiley & Sons: New York, 1991, Volumes 1–40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme A below illustrates one synthetic procedure usable to prepare specific compounds of formula (I) wherein $R^1$, $R^3$, $R^4$, m and n are as defined herein.

SCHEME A

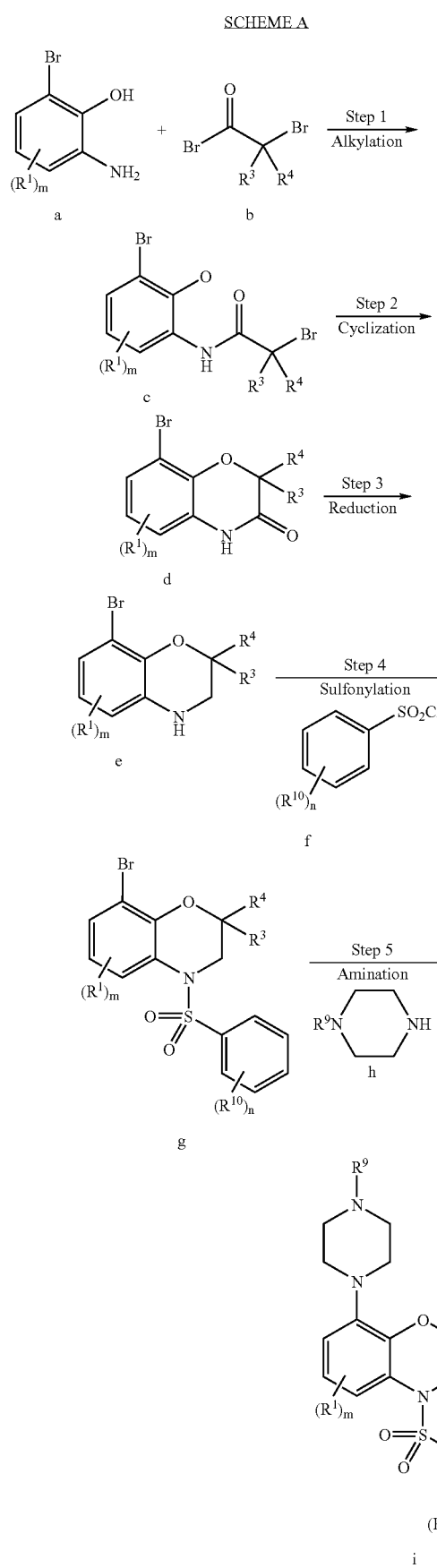

In step 1 of Scheme A, an ortho aminophenol a is N-alkylated by reaction with acid halide b to afford benzamide compound c. This reaction may be carried out in dry polar aprotic solvent at reduced temperatures in the presence of an amine base. Acid halide b may comprise, for example, 2-bromo-2-methyl propionyl bromide (providing $R^3$ and $R^4$ each as methyl), 2-bromo-2-(2-hydroxyethyl)-butyroyl bromide (providing $R^3$ and $R^4$ each as 2-hydroxyethyl), 2-bromo-2-(2-methoxyethyl)-propionyl bromide (providing $R^3$ as 2-methoxyethyl and $R^4$ as methyl), 1-bromo-cyclobutanecarbonyl bromide (providing $R^3$ and $R^4$ which together with their shared carbon form a cyclobutyl ring), and the like. The bromine groups on acid halide b may be replaced with chloro or other leaving groups in many instances.

In step 2, bemzamide compound c undergoes a cyclization to form benzoxazinone compound d. This cyclization may be achieved by heating benzamide compound c in the presence of mild base such as potassium carbonate under polar aprotic solvent conditions.

The benzoxazinone compound d of step 2 is reduced in step 3 to afford benzoxazine e. The reduction of step 4 may utilize, for example, reducing agents such as borane or borane complexes, sodium cyanoborohydride, Raney nickel/hydrazine, or the like.

In step 4, benzoxazine e undergoes a sulfonylation reaction by treatment with aryl sulfonyl halide f to yield arylsulfonyl benzoxazine g. The sulfonylation reaction of step 4 may be easily effected under polar aprotic solvent conditions in the presence of an amine base. The aryl sulfonyl halide f, it should be noted, may be replaced by heteroaryl sulfonyl chlorides such as pyridine sulfonyl chlorides, thiene sulfonyl chlorides, furan sulfonyl chlorides, or the like.

In step 5, an amination reaction is carried out wherein arylsulfonyl benzoxazine g is treated with piperazine compound h in the presence of a palladium catalyst under non-polar solvent conditions, to afford a piperazinyl arylsulfonyl benzoxazine i. The compound i is a compound of formula (I) in accordance with the invention, wherein X is N, Y is —$SO_2$—, $R^2$ is optionally substituted phenyl, and $R^5$, $R^6$, $R^7$ and $R^8$ are hydrogen. Compound i is more specifically a compound of formula (II), described above.

In instances where $R^9$ is hydrogen, BOC protection or other suitable protection strategies may be used to protect the corresponding ring nitrogen of piperazine i, and deprotection to remove this BOC or other protecting group may be carried out in step 5 following the amination reaction.

Many variations on the above procedure are possible and will suggest themselves to those skilled in the art upon review of this disclosure. One such variation, shown in Scheme B, may be used to provide compounds of formula (I) wherein Y is —$CH_2$— instead of —$SO_2$—.

SCHEME B

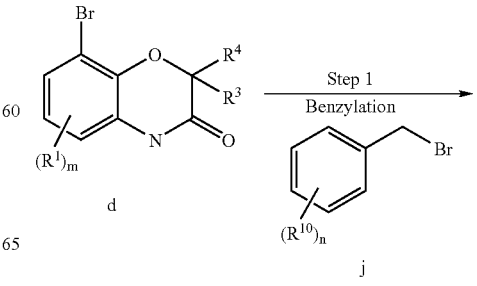

-continued

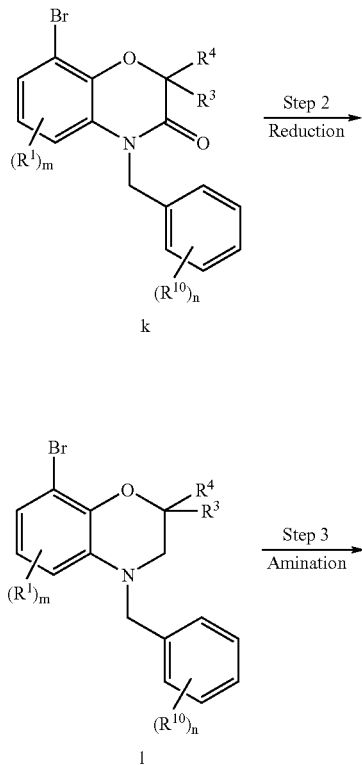

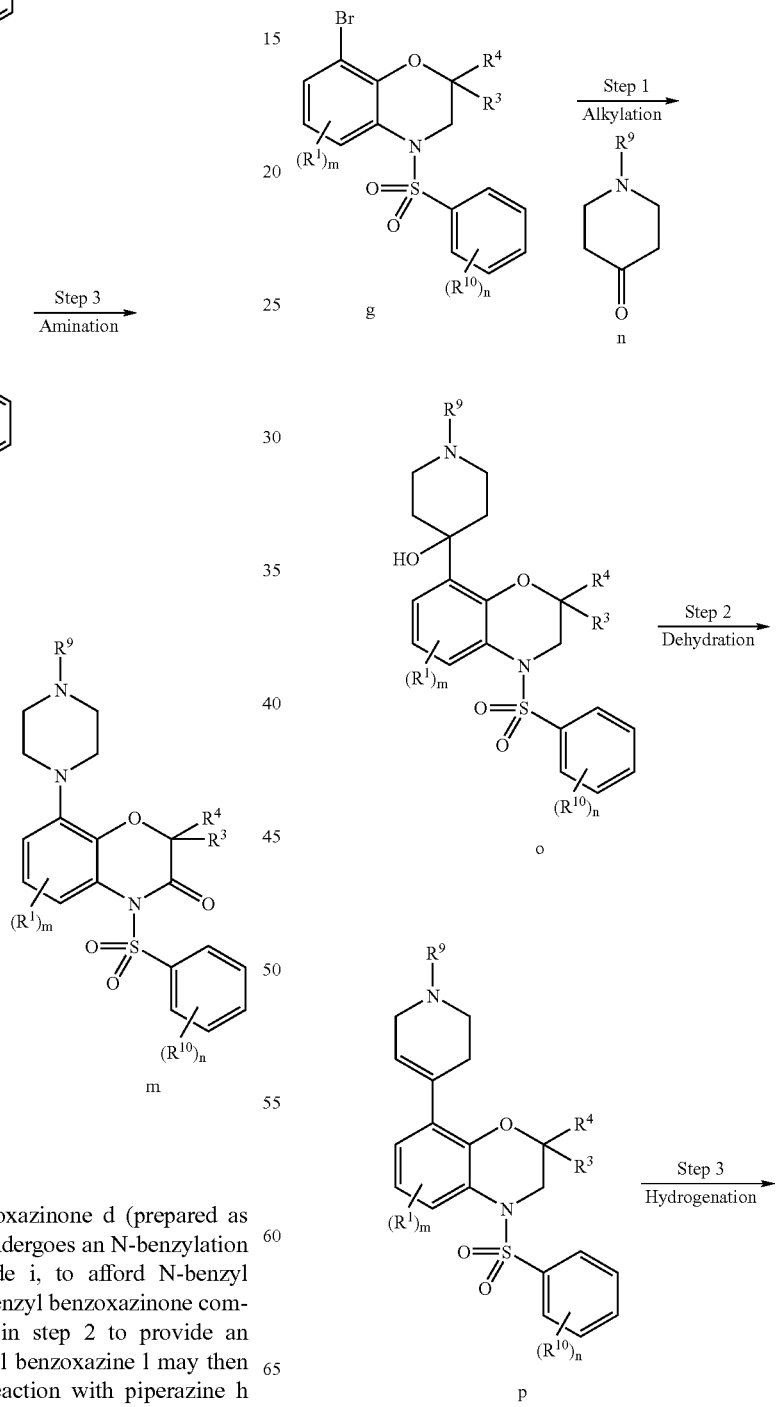

zoxazine m, which is a compound of formula (I) wherein X is N, Y is —$CH_2$—, $R^2$ is optionally substituted phenyl, and $R^5$, $R^6$, $R^7$ and $R^8$ are hydrogen. Where $R^9$ is hydrogen, a suitable protection/deprotection strategy may be utilized during the amination reaction as noted above.

Another variation on the procedure of Scheme A, shown in Scheme C, may be used to prepared compounds of formula (I) wherein X is CH instead of N.

SCHEME C

In step 1 of Scheme B, benzoxazinone d (prepared as described above in Scheme A), undergoes an N-benzylation by reaction with benzyl bromide i, to afford N-benzyl benzoxazinone compound k. N-benzyl benzoxazinone compound k may then be reduced in step 2 to provide an N-benzyl benzoxazine l. N-benzyl benzoxazine l may then in turn undergo amination by reaction with piperazine h (shown in Scheme A) to provide piperazinyl benzyl ben- -continued

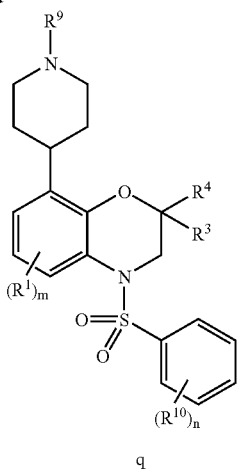

q

In step 1 of Scheme C, arylsulfonyl benzoxazine g (prepared as described above in step 4 of Scheme A) is treated with an alkyllithium reagent such n-butyl lithium under anhydrous polar aprotic conditions and dry ice/acetone temperature, to generate a lithiated intermediate (not shown) wherein the bromine group of compound g is replaced by lithium. This lithiated intermediate is then directly reacted in-situ with heterocyclic ketone n to effect an alkylation and provide a heterocyclyl-substituted arylsulfonyl benzoxazine o. The heterocyclic ketone n may comprise, for example, a piperidone as shown, or alternatively a pyrrolidinone or azepinone, all of which are commercially available. Where $R^9$ is hydrogen, Boc protection or other removable protection strategies may be used to protect the exposed nitrogen of heterocyclic ketone n and corresponding nitrogen on the heterocyclyl-substituted arylsulfonyl benzoxazine o.

In Step 2, the heterocyclyl-substituted arylsulfonyl benzoxazine o is dehydrated by treatment with mild acid to yield the compound p wherein the heterocyclyl moiety is partially unsaturated. In certain embodiments this dehydration may occur spontaneously, making step 2 unnecessary.

In Step 3, compound p of step 3 is hydrogenated to provide substituted benzoxazine compound q. This reaction may be achieved via hydrogenation using a platinum or palladium catalyst under mild ethanolic conditions. The benzoxazine compound q is a compound of formula (I) wherein X is CH, Y is —$SO_2$—, and $R^2$ is optionally substituted phenyl.

The procedure of Scheme C may also be used with N-benzyl benzoxazinone compound k in place of arylsulfonyl benzoxazine g, to afford compounds of formula (I) wherein X is CH, Y is —$CH_2$—, and $R^2$ is optionally substituted phenyl.

More specific details for producing Compounds of Formula I are described in the Examples section below.

Utility

The compounds of the invention have affinity for one or more 5-hydroxytryptamine receptors, including 5-HT1, 5-HT2, 5-HT3, 5-HT4, 5-HT5, 5-HT6, and/or 5-HT7. The compounds in general have selective 5-HT6 receptor affinity and as such are expected to be useful in the treatment of certain CNS disorders such as Parkinson's disease, Huntington's disease, anxiety, depression, manic depression, psychoses, epilepsy, obsessive compulsive disorders, mood disorders, migraine, Alzheimer's disease (enhancement of cognitive memory), sleep disorders, feeding disorders such as anorexia, bulimia and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain gastrointestinal (GI) disorders such as functional bowel disorder.

Testing

The pharmacology of the compounds of this invention was determined by art recognised procedures. The in vitro techniques for determining the affinities of test compounds at the 5-HT6 receptor in radioligand binding and functional assays are described in Example 4.

Administration and Pharmaceutical Composition

The present invention includes pharmaceutical compositions comprising at least one compound of the present invention, or an individual isomer, racemic or non-racemic mixture of isomers or a pharmaceutically acceptable salt or solvate thereof, together with at least one pharmaceutically acceptable carrier, and optionally other therapeutic and/or prophylactic ingredients.

In general, the compounds of the present invention will be administered in a therapeutically effective amount by any of the accepted modes of administration for agents that serve similar utilities. Suitable dosage ranges are typically 1–500 mg daily, preferably 1–100 mg daily, and most preferably 1–30 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this Application, to ascertain a therapeutically effective amount of the compounds of the present invention for a given disease.

In general, compounds of the present invention will be administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. The preferred manner of administration is generally oral using a convenient daily dosage regimen which can be adjusted according to the degree of affliction.

A compound or compounds of the present invention, together with one or more conventional adjuvants, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the present invention may be formulated in a wide variety of oral administration dosage forms. The pharmaceutical compositions and dosage forms may comprise a compound or compounds of the present invention or pharmaceutically acceptable salts thereof as the active component. The pharmaceutically acceptable carriers may be either solid or liquid. Solid form preparations include powders, tablets, pills, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges may be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylazacycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in Examples 6–12.

EXAMPLES

The following preparations and examples are given to enable those skilled in the art to more clearly understand and to practice the present invention. They should not be considered as limiting the scope of the invention, but merely as being illustrative and representative thereof.

Example 1

4-(2-Fluoro-benzenesulfonyl)-2,2-dimethyl-8-piperazin-1-yl-3,4-dihydro-2H-benzo[1,4]oxazine This example illustrates a method for producing compounds of formula (I) using the synthetic procedure of Scheme D below.

SCHEME D

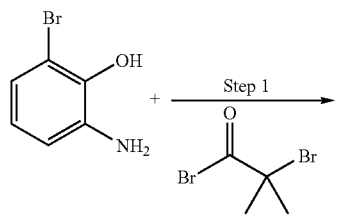

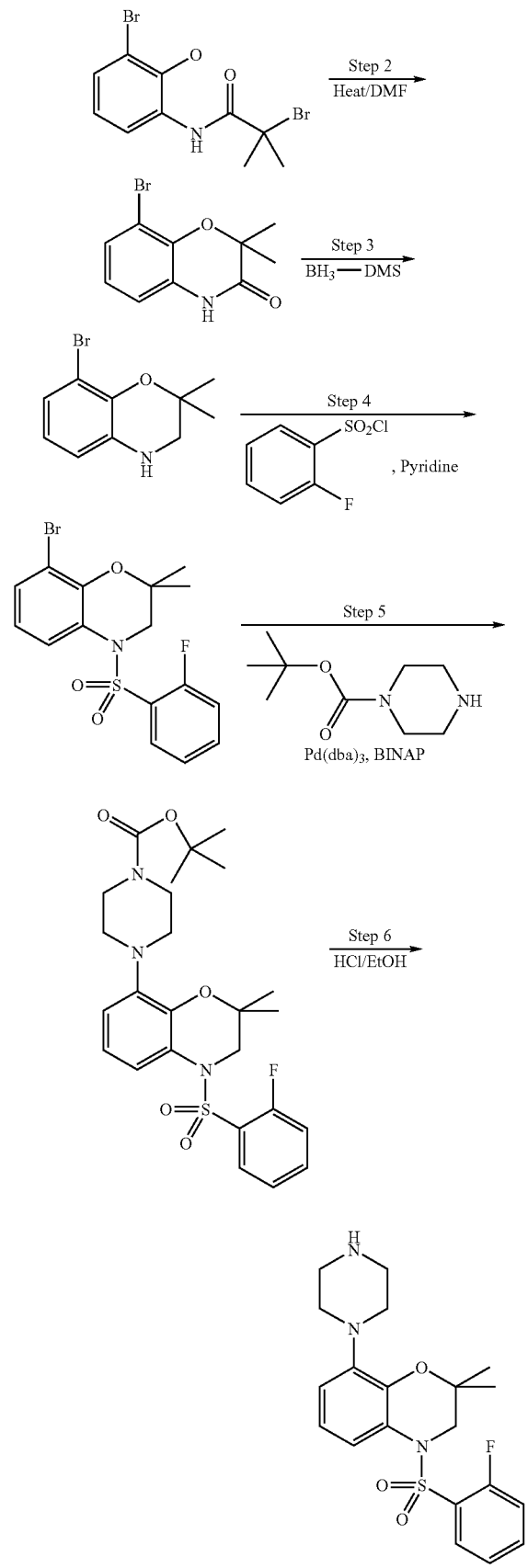

Step 1

2-Bromo-N-(3-bromo-2-hydroxy-phenyl)-2-methyl-propionamide

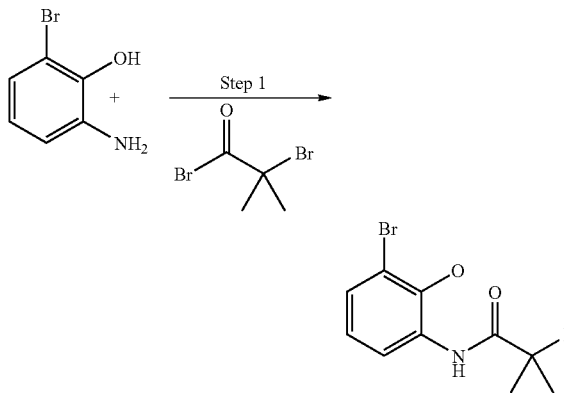

Pyridine (1.8 ml, 22.3 mmol) was added to a solution of 2-amino-6-bromo-phenol (4.198 g, 22.3 mmol) in dry $CH_2Cl_2$ 200 ml). The mixture was cooled in ice and then a solution of 2-bromo-2-methyl-propionylbromide (2.8 ml, 22.6 mmol) was added slowly. The mixture was stirred at the room temperature for an hour and was poured into $CH_2Cl_2$ and water. The organic layer was washed with water, dried and concentrated in vacuo to yield crude 2-bromo-N-(3-bromo-2-hydroxy-phenyl)-2-methyl-propionamide, which was used directly in step 2 without further purification.

Step 2

8-Bromo-2,2-dimethyl-4H-benzo[1,4]oxazin-3-one

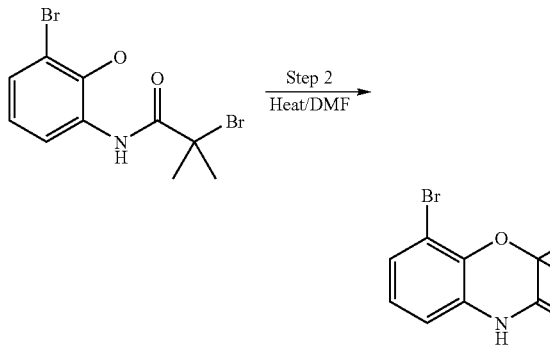

The 2-bromo-N-(3-bromo-2-hydroxy-phenyl)-2-methyl-propionamide of step 1 was dissolved in DMF (200 ml), and to the DMF solution was added to $K_2CO_3$ (6.3 g, 45.58 mmol). The mixture was heated overnight at 150° C., then cooled and poured into a mixture of water/ethyl acetate. The organic fraction was washed with brine. After drying over $MgSO_4$, the organic fraction was concentrated in vacuo and resulting brown residue was purified by flash chromatography to give 8-bromo-2,2-dimethyl-4H-benzo[1,4]oxazin-3-one as a white solid (84.6%). MS: (M–H)⁻ 256.

Step 3

8-Bromo-2,2-dimethyl-3,4-dihydro-2H-benzo[1,4]oxazine

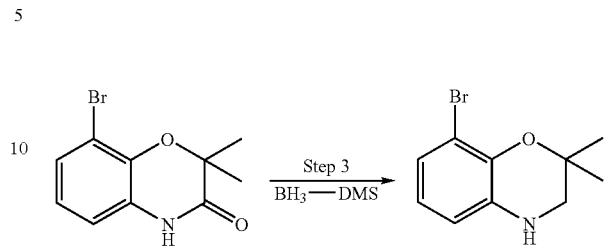

8-Bromo-2,2-dimethyl-4H-benzo[1,4]oxazin-3-one from step 2 (768.30 mg, 3.0 mmol) was dissolved in dry tetrahydrofuran (THF) and the solution was heated to reflux. 0.3 ml of 10M borane dimethyl sulfide (BH3.DMS) in THF was added drop-wise to the reaction mix, and the reaction mix was kept heated under reflux for 1 hour. A solution of 10% ethanolic HCl was then added drop-wise to the reaction mix until a white precipitate appeared, after which refluxing was continued for 10 minutes. The reaction mix was cooled, and the precipitate was removed by filtration, washed with ether, and air dried to yield 770 mg of 8-bromo-2,2-dimethyl-3,4-dihydro-2H-benzo[1,4]oxazine hydrochloride (92%) as a white solid. MS: (M+H) 280.

Step 4

8-Bromo-4-(2-fluoro-benzenesulfonyl)-2,2-dimethyl-3,4-dihydro-2H-benzo[1,4]oxazine

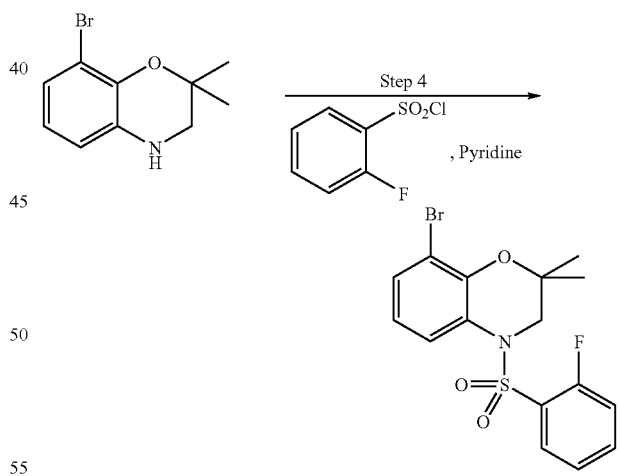

8-Bromo-2,2-dimethyl-3,4-dihydro-2H-benzo[1,4]oxazine hydrochloride (518 mg, 2.14 mmol) was dissolved in 5 ml methylene chloride, to which pyridine (253.85 g, 3.21 mmol) was then added. The reaction mix was stirred at room temperature, and 2-fluorobenzenesulfonyl chloride (416.37 mg, 2.14 mmol) was added drop-wise to the reaction mix, after which stirring at room temperature was continued for 2 hours. The reaction mix was then heated to reflux for 1 hour, and cooled to room temperature. The reaction mix was diluted with 5 ml of methylene chloride and 10% aqueous HCl was added. The organic layer was separated, washed with water, then saturated NaHCO$_3$, and dried (Na$_2$SO$_4$). Solvent was removed under reduced pressure, and the residue was purified via flash chromatography (EtOAc in hexane, 5% to 20%) to afford 610 g (71.3%) of 8-bromo-4-(2-fluoro-benzenesulfonyl)-2,2-dimethyl-3,4-dihydro-2H-benzo[1,4]oxazine as an oil which solidified upon standing. MP: 108.0–110.1° C. MS: (M+H) 401.

Step 5

4-[4-(2-Fluoro-benzenesulfonyl)-2,2-dimethyl-3,4-dihydro-2H-benzo[1,4]oxazin-8-yl]-piperazine-1-carboylic acid tert-butyl ester

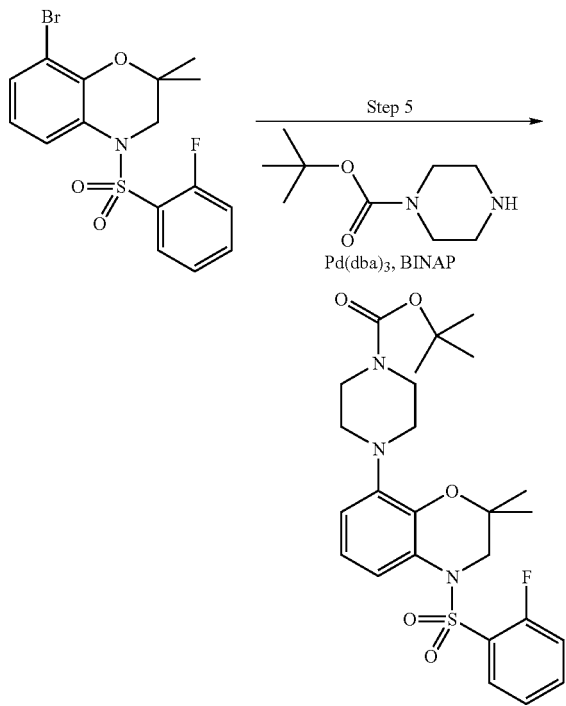

A solution of 8-bromo-4-(2-fluoro-benzenesulfonyl)-2,2-dimethyl-3,4-dihydro-2H-benzo[1,4]oxazine (450 mg, 1.124 mmol) and 1-Boc-piperazine (209.4 mg, 1.124 mmol) in 5 mL of toluene was added to a warm, degassed mixture of Pd$_2$(dba)$_3$(Tris(dibenzylideneacetone)dipalladium(0), 20.59 mg, 0.022 mmol), BINAP (2,2'-bis(diphenylphosphino)-1,1'-binaphthyl, 35.0 mg, 0.056 mmol) and NaOt-Bu (151.26 mg, 1.57 mmol) in 5 ml of toluene. With stirring, the solution was heated at 90° C. for 2 hours, and then allowed to cool to room temperature. Ethyl acetate was added to the reaction which was then filtered through celite. The filtrate was washed with water (2×15 ml), brine (1×15 ml), and dried over MgSO$_4$, after which the organic fraction was concentrated in vacuo. The resulting residue was purified by flash chromatography (15%–30% Ethyl acetate/Hexane) to give 470 mg (0.93 mmol) of 4-[4-(2-fluoro-benzenesulfonyl)-2,2-dimethyl-3,4-dihydro-2H-benzo[1,4]oxazin-8-yl]-piperazine-1-carboxylic acid tert-butyl ester. MS: (M+H) 506.

Step 6

4-(2-Fluoro-benzenesulfonyl)-2,2-dimethyl-8-pipierazin-1-yl-3,4-dihydro-2H-benzo[1,4]oxazine

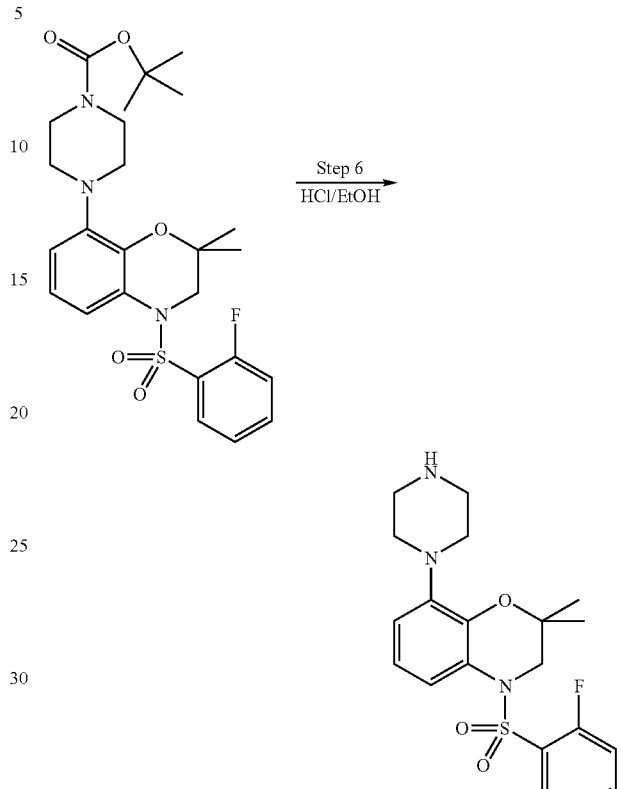

4-[4-(2-Fluoro-benzenesulfonyl)-2,2-dimethyl-3,4-dihydro-2H-benzo[1,4]oxazin-8-yl]-piperazine-1-carboxylic acid tert-butyl ester (470 mg, 0.93 mmol) was dissolved in 3 ml ethanol. To this solution was added 1 ml of 10% ethanolic hydrochloric acid solution. The mixture was heated at 100° C. (steam bath) for 15 minutes, and then cooled to room temperature at which time a white crystalline solid formed. The solid was collected by filtration and dried at 70° C. under vacuum to provide 160 mg of 4-(2-fluoro-benzenesulfonyl)-2,2-dimethyl-8-piperazin-1-yl-3,4-dihydro-2H-benzo[1,4]oxazine as a hydrochloride salt. MP: 222.9–227.1° C. MS: (M+H) 479.

The solution was allowed to cool to room temperature and 0.115 g. of 4-benzyl-8-piperazin-1-yl-4H-benzo[1,4]oxazin-3-one hydrochloride salt is collected as a light yellow powder after filtering and drying in a vacuum oven. MS: 324 (M+H)$^+$, mp=235.9–236.2° C.

Several additional compounds were prepared using the above procedure by replacing 2-fluorobenzenesulfonyl chloride in step 4 with the appropriate substituted benzenesulfonyl chlorides or pyridine sulfonyl chloride, and/or replacing 2-bromo-2-methyl-propionylbromide in step 2 with 1-bromo-cyclobutanecarbonyl bromide. These compounds are shown in Table 1 above.

Example 5

This example illustrates in vitro radioligand binding studies of compound of formula (I).

The binding activity of compounds of this invention in vitro was determined as follows. Duplicate determinations of ligand affinity are made by competing for binding of [³H]LSD in cell membranes derived from HEK293 cells stably expressing recombinant human 5-HT6 receptor. This cell line was prepared by the method described by Monsma et al., *Molecular Pharmacology*, Vol. 43 pp. 320–327 (1993).

All determinations were made in assay buffer containing 50 mM Tris-HCl, 10 mM MgSO₄, 0.5 mM EDTA, 1 mM ascorbic acid, pH 7.4 at 37° C., in a 250 microliter reaction volume. Assay tubes containing [³H] LSD (5 nM), competing ligand, and membrane were incubated in a shaking water bath for 60 min. at 37° C., filtered onto Packard GF-B plates (pre-soaked with 0.3% PEI) using a Packard 96 well cell harvester and washed 3 times in ice cold 50 mM Tris-HCl. Bound [³H] LSD was determined as radioactive counts per minute using Packard TopCount.

Displacement of [3H]LSD from the binding sites was quantified by fitting concentration-binding data to a 4-parameter logistic equation:

$$\text{binding} = \text{basal} + \left( \frac{B\max - \text{basal}}{1 + 10^{-\text{Hill}(\log[\text{ligand}] - \log IC_{50})}} \right)$$

where Hill is the Hill slope, [ligand] is the concentration of competing radioligand and $IC_{50}$ is the concentration of radioligand producing half-maximal specific binding of radioligand. The specific binding window is the difference between the Bmax and the basal parameters.

Using the procedures of Example 5, compounds of formula (I) were tested and found to be 5-HT6 antagonists. Surprisingly, compounds of formula (I) wherein $R^3$ and $R^4$ are methyl, or where $R^3$ and $R^4$ together form a cyclobutyl group, exhibit 5-HT6 affinity of about one half log order or more better than the corresponding compounds wherein $R^3$ and $R^4$ are hydrogen. This unexpected result is more fully illustrated by the pKi values shown Table 2.

| Compound | $R^3, R^4$ | pKi |
|---|---|---|
| 4-(2-Fluoro-benzenesulfonyl)-2,2-dimethyl-8-piperazin-1-yl-3,4-dihydro-2H-benzo[1,4]oxazine | $R^3, R^4 =$ methyl | 9.68 |
| 4-(2-Fluoro-benzenesulfonyl)-8-piperazin-1-yl-3,4-dihydro-2H-benzo[1,4]oxazine | $R^3, R^4 =$ hydrogen | 8.90 |
| 4-(3-Fluoro-benzenesulfonyl)-2,2,6-trimethyl-8-piperazinyl-yl-3,4-dihydro-2H-benzo[1,4]oxazine | $R^3, R^4 =$ methyl | 9.39 |
| 4-(3-Fluoro-benzenesulfonyl)-6-methyl-8-piperazin-1-yl-3,4-dihydro-2H-benzo[1,4]oxazine | $R^3, R^4 =$ hydrogen | 8.70 |
| 6-Fluoro-4-(2-fluoro-benzenesulfonyl)-2,2-dimethyl-8-piperazin-1-yl-3,4-dihydro-2H-benzo[1,4]oxazine | $R^3, R^4 =$ methyl | 9.68 |
| 6-Fluoro-4-(2-fluoro-benzenesulfonyl)-8-piperazin-1-yl-3,4-dihydro-2H-benzo[1,4]oxazine | $R^3, R^4 =$ hydrogen | 9.14 |
| 4-(3-Fluoro-benzenesulfonyl)-2,2-spiro-cyclobutan-8-piperazin-1-yl-3,4-dihydro-2H-benzo[1,4]oxazine | $R^3, R^4$ form cyclobutyl | 8.93 |
| 4-(3-Fluoro-benzenesulfonyl)-8-piperazin-1-yl-3,4-dihydro-2H-benzo[1,4]oxazine | $R^3, R^4 =$ hydrogen | 7.95 |
| 4-(3-Chloro-benzenesulfonyl)-2,2-spiro-cyclobutan-8-piperazin-1-yl-3,4-dihydro-2H-benzo[1,4]oxazine | $R^3, R^4$ form cyclobutyl | 9.30 |
| 4-(2-Chloro-benzenesulfonyl)-8-piperazin-1-yl-3,4-dihydro-2H-benzo[1,4]oxazine | $R^3, R^4 =$ hydrogen | 8.67 |

Example 6

The cognition-enhancing properties of compounds of the invention may be in a model of animal cognition: the object recognition task model. 4-month-old male Wistar rats (Charles River, The Netherlands) were used. Compounds were prepared daily and dissolved in physiological saline and tested at three doses. Administration was always given i.p. (injection volume 1 ml/kg) 60 minutes before T1. Scopolamine hydrobromide was injected 30 minutes after compound injection. Two equal testing groups were made of 24 rats and were tested by two experimenters. The testing order of doses was determined randomly. The experiments were performed using a double blind protocol. All rats were treated once with each dose condition. The object recognition test was performed as described by Ennaceur, A., Delacour, J., 1988, A new one-trial test for neurobiological studies of memory in rats. 1: Behavioral data. *Behav. Brain Res.* 31, 47–59.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound of the formula (I):

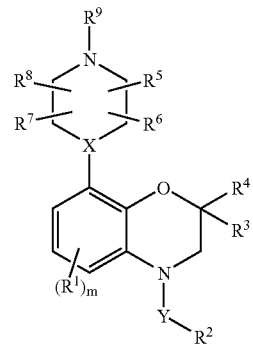

or a pharmaceutically acceptable salt thereof, wherein:
  m is from 0 to 3;
  X is N or CH;
  Y is —SO₂— or —CH₂—;
  each $R^1$ is independently halo, alkyl, haloalkyl, alkoxy, cyano, hydroxyalkyl, alkoxyalkyl, —SO₂$R^a$, —C(=O)—NR$^b$R$^c$, —SO₂—NR$^b$R$^c$, —SR$^b$, —N(R$^b$)—C(=O)—R$^c$, —C(=O)—R$^b$, or —N(R$^b$)—SO₂—R$^a$,
    where
      each $R^a$ is independently alkyl or haloalkyl, and
      each of $R^b$ and $R^c$ is independently hydrogen, alkyl, or haloalkyl,
  $R^2$ is aryl or heteroaryl;
  each of $R^3$ and $R^4$ is independently alkyl, hydroxyalkyl or alkoxyalkyl, or $R^3$ and $R^4$ together with the carbon to which they are attached may form a cyclobutyl group; and
  each of $R^5$, $R^6$, $R^7$, $R^8$ and $R^9$ is independently hydrogen or alkyl, or $R^9$ and one of $R^5$, $R^6$, $R^7$, or $R^8$ together with the atoms to which they are attached form a ring with 5 to 7 ring atoms.

2. The compound of claim 1, wherein Y is —SO₂—.

3. The compound of claim 2, wherein X is N.

4. The compound of claim 3, wherein R² is aryl.

5. The compound of claim 3, wherein R² is optionally substituted phenyl.

6. The compound or claim 5, wherein R³ and R⁴ are alkyl.

7. The compound of claim 6, wherein m is 0 or 1.

8. The compound of claim 7, wherein R¹ is halo, alkyl, haloalkyl, alkoxy, cyano, hydroxyalkyl, or alkoxyalkyl.

9. The compound of claim 8, wherein R² is halophenyl.

10. The compound of claim 9, wherein R² is 2-helophenyl, 3-halophenyl or 4-halophenyl.

11. The compound of claim 10, wherein R² is 2-fluorophenyl or 2-chlorophenyl.

12. The compound of claim 6, wherein R³ and R⁴ are methyl.

13. The compound of claim 6, wherein R³ and R⁴ together with the carbon to which they are attached may form a cyclic group with 3 to 6 ring atoms that optionally includes a heteroatom selected from N, O and S.

14. The compound of claim 6, wherein R³ and R⁴ together with the carbon to which they are attached form a cyclobutyl group.

15. The compound of claim 1, wherein said compound is of the formula (II):

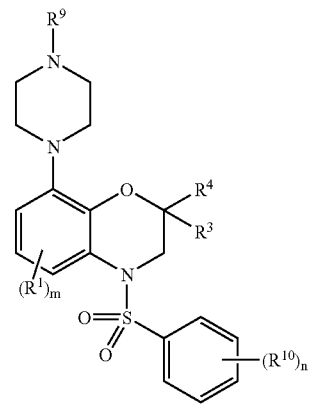

wherein:
n is from 0 to 5;
each R¹⁰ is independently alkyl, halo, haloalkyl, alkoxy or cyano; and
m, R¹, R³, R⁴ and R⁹ are as recited in claim 1.

16. The compound of claim 15, wherein n is 0 or 1.

17. The compound of claim 16, wherein R¹⁰ is halo.

18. A pharmaceutical composition comprising an effective amount of the compound of claim 1 in admixture with a pharmaceutically acceptable carrier.

* * * * *